US012746327B2

(12) United States Patent
Mccaffrey et al.

(10) Patent No.: US 12,746,327 B2
(45) Date of Patent: Sep. 29, 2026

(54) ESTABLISHING AND MAINTAINING VACUUM IN THE RESERVOIR OF A DRUG DELIVERY DEVICE

(71) Applicant: INSULET CORPORATION, Acton, MA (US)

(72) Inventors: Maureen Mccaffrey, Arlington, MA (US); Soroush Kamrava, Everett, MA (US); Ian Mclaughlin, Groton, MA (US)

(73) Assignee: INSULET CORPORATION, Acton, MA (US)

( * ) Notice: Subject to any disclaimer, the term of this patent is extended or adjusted under 35 U.S.C. 154(b) by 917 days.

(21) Appl. No.: 18/047,071

(22) Filed: Oct. 17, 2022

(65) Prior Publication Data

US 2023/0120570 A1 Apr. 20, 2023

Related U.S. Application Data

(60) Provisional application No. 63/256,936, filed on Oct. 18, 2021.

(51) Int. Cl.
*A61M 5/142* (2006.01)

(52) U.S. Cl.
CPC ... *A61M 5/142* (2013.01); *A61M 2005/14252* (2013.01); *A61M 2209/04* (2013.01)

(58) Field of Classification Search
CPC ........ A61M 5/142; A61M 2005/14252; A61M 2209/04; A61M 2205/07; A61M 5/36; A61M 5/145; A61M 5/14248; A61M 2005/3114; B65B 3/003; A61J 1/1493
See application file for complete search history.

(56) References Cited

U.S. PATENT DOCUMENTS

| | | | | |
|---|---|---|---|---|
| 4,991,743 | A | 2/1991 | Walker | |
| 5,368,570 | A | 11/1994 | Thompson et al. | |
| 5,741,242 | A * | 4/1998 | Kriesel | A61M 5/152 141/318 |
| 5,906,592 | A | 5/1999 | Kriesel et al. | |
| 6,740,059 | B2 | 5/2004 | Flaherty | |
| 7,137,964 | B2 | 11/2006 | Flaherty | |

(Continued)

FOREIGN PATENT DOCUMENTS

| | | | |
|---|---|---|---|
| CN | 107096091 | A | 8/2017 |
| EP | 0789146 | A1 | 8/1997 |

(Continued)

OTHER PUBLICATIONS

European Search Report and Written Opinion, Application No. EP02768908, dated Apr. 30, 2010.

(Continued)

*Primary Examiner* — Theodore J Stigell
(74) *Attorney, Agent, or Firm* — Goodwin Procter LLP

(57) ABSTRACT

Disclosed herein are structures for ensuring that the reservoir of drug delivery device is free from any residual air before the device is filled with a liquid drug and put into use. The structures described herein are designed to prevent air from entering the reservoir during the pendency of a shelf life of the drug delivery device and/or to remove any residual air that has entered the reservoir of the drug delivery device prior to it being filled with the liquid drug.

10 Claims, 11 Drawing Sheets

(56) References Cited

U.S. PATENT DOCUMENTS

| | | | |
|---|---|---|---|
| 7,303,549 | B2 | 12/2007 | Flaherty |
| 8,734,396 | B2 | 5/2014 | Wyss |
| 2003/0198558 | A1 | 10/2003 | Nason et al. |
| 2004/0115068 | A1 | 6/2004 | Hansen et al. |
| 2007/0255260 | A1 | 11/2007 | Haase |
| 2011/0108158 | A1 | 5/2011 | Huwiler et al. |
| 2011/0319814 | A1 | 12/2011 | Sullivan et al. |
| 2017/0290975 | A1 | 10/2017 | Barmaimon et al. |

FOREIGN PATENT DOCUMENTS

| | | | |
|---|---|---|---|
| EP | 1065378 | A2 | 1/2001 |
| EP | 2229970 | A1 | 9/2010 |
| EP | 2556815 | A1 | 2/2013 |
| WO | 2012065780 | A2 | 5/2012 |
| WO | 2013149186 | A1 | 10/2013 |

OTHER PUBLICATIONS

International Search Report and Written Opinion, Application No. PCT/US2019/042233, mailed Jan. 3, 2020, 14 pages.
International Search Report and Written Opinion, Application No. PCT/US2021/060148, mailed Mar. 17, 2022, 17 pages.
International Search Report and Written Opinion, Application No. PCT/US2022/016713, mailed Aug. 5, 2022, 19 pages.

* cited by examiner

100

ESTABLISHING AND MAINTAINING VACUUM IN THE RESERVOIR OF A DRUG DELIVERY DEVICE

RELATED APPLICATIONS

This application claims the benefit of U.S. Provisional Patent Application No. 63/256,936, filed Oct. 18, 2021, the contents of which are incorporated herein by reference in their entirety.

BACKGROUND

Many conventional drug delivery systems, including, for example, wearable drug delivery devices, include a drug container, often referred to as a reservoir, that stores a liquid drug for delivery to a user in accordance with an algorithm. In many embodiments, the reservoir of the drug delivery device may be filled by the user with a liquid drug before the drug delivery device is attached to the body of the user.

In other embodiments of drug delivery devices, the reservoir may be a collapsible container composed of a flexible material, wherein the reservoir is initially collapsed, but expands when filled with a liquid drug and which thereafter contracts as the liquid drug is dispensed to the user.

With embodiments of reservoirs having either a rigid shell or a collapsible container, there is a risk of air residing within the reservoir prior to the reservoir being filled by the user. If this is not mitigated, there can be negative clinical implications, as well as implications for the operation of the pumping mechanism.

The clinical implication is that the user may receive air in place of the liquid drug and, hence, would not be receiving the correct therapy dose. In a reciprocating pump, the air bubble could get trapped in such a way that every minimum dose increment is decreased due to the air bubble. Because air is a compressible fluid, if the air bubble is large enough, it could hinder operation of the pump such that the user receives no therapy at all.

An example of a typical wearable drug delivery device is shown in FIG. 1B as reference number 102. In such devices it would be desirable to provide mechanisms to mitigate the risk of air entering the reservoir during the pendency of the shelf life of the device or, alternatively or in addition, to provide a mechanism to evacuate the air from the reservoir prior to filling of the reservoir with the liquid drug by the user.

SUMMARY OF THE INVENTION

The embodiments of the invention described herein address the problems identified above. In a first aspect of the invention, the goal is to prevent air from entering the reservoir during the shelf life of the device. In one embodiment of the first aspect of the invention, multiple layers of a barrier film are used to section off the outlet port from the reservoir to the pump. If necessary, the layers of the barrier film can be placed such that multiple layers of barrier film must be punctured when the user inserts the fill needle to fill the reservoir with the liquid drug. In a second embodiment of the first aspect of the invention, a mechanism is provided that causes the fluid path to puncture a layer of foil to connect the fluid path with the reservoir.

In various embodiments of the invention, the reservoir may be composed of a rigid outer shell having a foil liner, wherein, when the reservoir is filled with the liquid drug, the foil liner is displaced from the interior surface of the rigid outer shell and the liquid drug is able to occupy the space between the displaced foil liner and the rigid outer shell.

In embodiments of the first aspect of the invention, it could be challenging to keep the reservoir in the evacuated state during the pendency of an extended shelf life. If there is vacuum pressure inside the reservoir, the higher atmospheric pressure outside of the reservoir will cause air to attempt to enter the reservoir. Plastic or rubber films that may be used in the construction of the flexible reservoir have some permeability to air. Over an extended period (e.g., the shelf life) the reservoir may not be able to hold a vacuum. Additionally, it may be challenging to get a perfect hermetic seal in the fluid ports, especially if rubber compression seals are used (e.g., O-rings, septa, etc.).

Therefore, in a second aspect of the invention, the goal is to evacuate any air that may have entered the reservoir prior to the filling of the reservoir with the liquid drug. One embodiment of the second aspect of the invention provides a breakaway, spring-loaded attachment that would be connected to the drug delivery device to pull air from the reservoir immediately prior to filling the reservoir with the liquid drug. Before filling, the user removes the spring-loaded attachment by breaking it away from the drug delivery device and discards it.

As would be realized by one of ordinary skill in the art, either or both aspects of the invention may be implemented in any given embodiment of the invention.

DETAILED DESCRIPTION

Several exemplary embodiments are shown herein; however, it should be realized that aspects of the invention are not meant to be limited thereby but are instead meant to encompass the novel aspects of the various embodiments. Variations of the exemplary embodiments providing the same functionality are intended to be included within the scope of the invention. Further, it should be realized that various aspects of the invention may be used either individually or in any combination.

Various embodiments of the present invention include systems and methods for delivering a medication to a user using a drug delivery device (sometimes referred to herein as a "pod"), either autonomously, or in accordance with a wireless signal received from an electronic device. In various embodiments, the electronic device may be a user device comprising a smartphone, a smart watch, a smart necklace, a module attached to the drug delivery device, or any other type or sort of electronic device that may be carried by the user or worn on the body of the user and that executes an algorithm that computes the times and dosages of delivery of the medication.

For example, the user device may execute an "artificial-pancreas" algorithm that computes the times and dosages of delivery of insulin. The user device may also be in communication with a sensor, such as a glucose sensor, that collects data on a physical attribute or condition of the user, such as a glucose level. The sensor may be disposed in or on the body of the user and may be part of the drug delivery device or may be a separate device.

Alternatively, the drug delivery device may be in communication with the sensor in lieu of or in addition to the communication between the sensor and the user device. The communication may be direct (if, e.g., the sensor is integrated with or otherwise a part of the drug delivery device) or remote/wireless (if, e.g., the sensor is disposed in a different housing than the drug delivery device). In these embodiments, the drug delivery device contains computing hardware (e.g., a processor, memory, firmware, etc.) that executes some or all of the algorithm that computes the times and dosages of delivery of the medication.

Figure 1A:
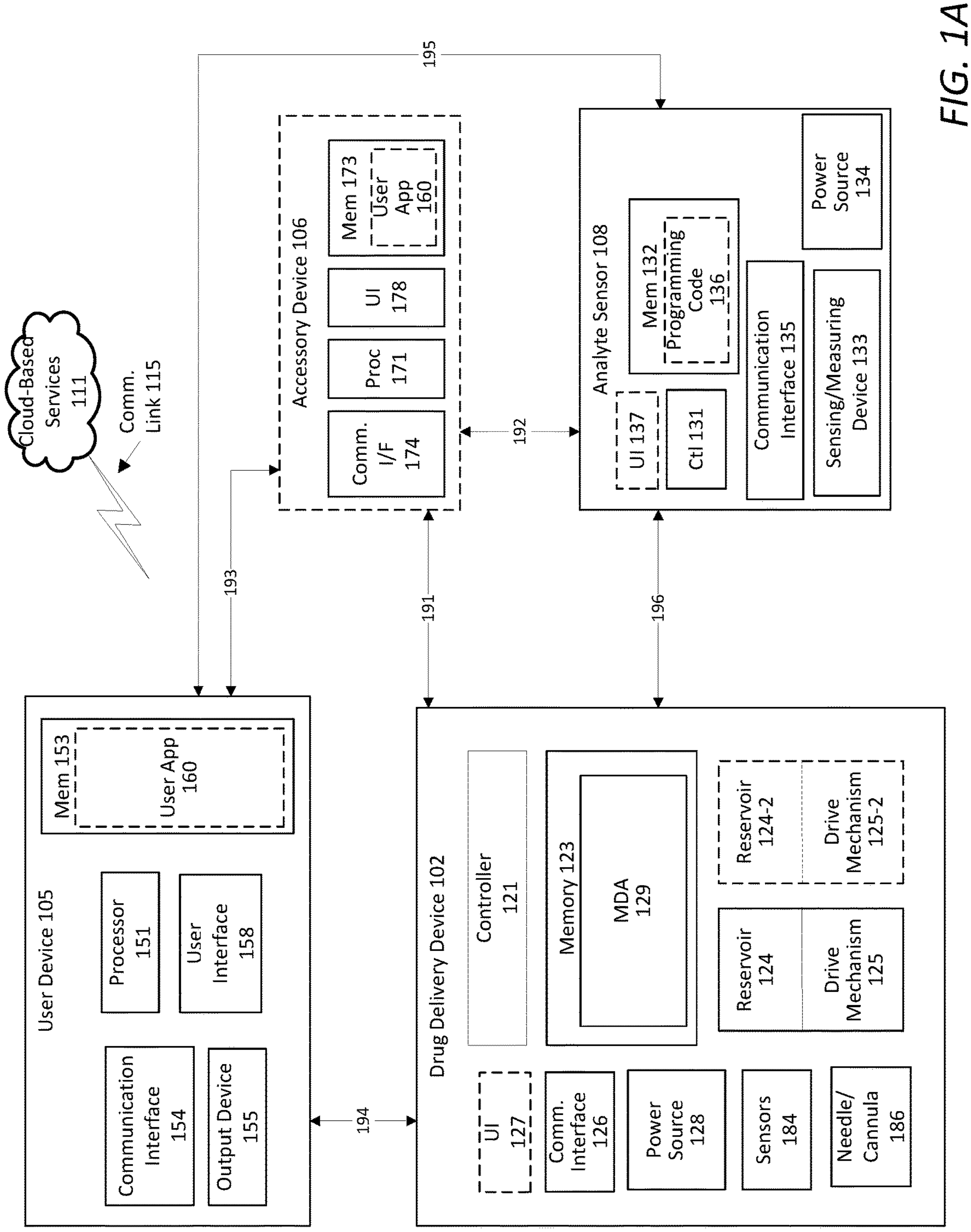
FIG. 1A illustrates a functional block diagram of an exemplary system suitable for implementing the systems and methods disclosed herein.
Figure 1B:
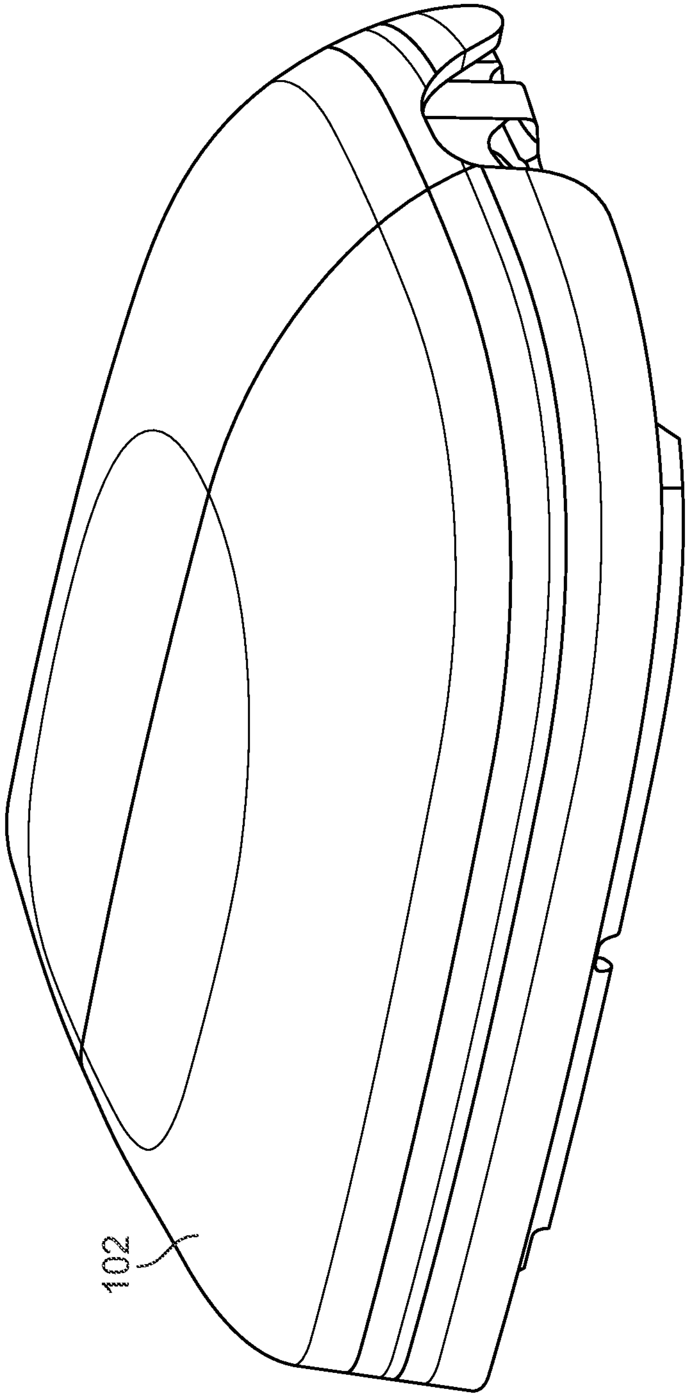
FIG. 1B is a prior art wearable drug delivery device.

FIG. 1A illustrates a functional block diagram of an exemplary drug delivery system 100 suitable for implementing the systems and methods described herein. The drug delivery system 100 may implement (and/or provide functionality for) a medication delivery algorithm, such as an artificial pancreas (AP) application, to govern or control the automated delivery of a drug or medication, such as insulin, to a user (e.g., to maintain euglycemia—a normal level of glucose in the blood). The drug delivery system 100 may be an automated drug delivery system that may include a drug delivery device 102 (which may be wearable), an analyte sensor 108 (which may also be wearable), and a user device 105.

Drug delivery system 100, in an optional example, may also include an accessory device 106, such as a smartwatch, a personal assistant device, or the like, which may communicate with the other components of system 100 via either a wired or wireless communication links 191-193.

User Device

The user device 105 may be a computing device such as a smartphone, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 to manage a user's blood glucose levels and for controlling the delivery of the drug, medication, or therapeutic agent to the user, as well for providing other functions, such as calculating carbohydrate-compensation dosage, a correction bolus dosage and the like as discussed below. The user device 105 may be used to program, adjust settings, and/or control operation of drug delivery device 102 and/or the analyte sensor 103 as well as the optional smart accessory device 106.

The processor 151 may also be configured to execute programming code stored in device memory 153, such as the user app 160. The user app 160 may be a computer application that is operable to deliver a drug based on information received from the analyte sensor 103, the cloud-based services 111 and/or the user device 105 or optional accessory device 106. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 is an AP application, the processor 151 is also configured to execute a diabetes treatment plan (which may be stored in a memory) that is managed by user app 160. In addition to the functions mentioned above, when user app 160 is an AP application, it may further provide functionality to determine a carbohydrate-compensation dosage, a correction bolus dosage and determine a basal dosage according to a diabetes treatment plan. In addition, as an AP application, user app 160 provides functionality to output signals to the drug delivery device 102 via communications interface 154 to deliver the determined bolus and basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

Drug Delivery Device

In various exemplary embodiments, drug delivery device 102 may include a reservoir 124 and drive mechanism 125, which are controllable by controller 121, executing a medication delivery algorithm (MDA) 129 stored in memory 123. Alternatively, controller 121 may act to control reservoir 124 and drive mechanism 125 based on signals received from user app 160 executing on a user device 105 and communicated to drug delivery device 102 via communication link 194. Drive mechanism 125 operates to longitudinally translate a plunger through the reservoir, such as to force the liquid drug through an outlet fluid port to needle/cannula 186.

In an alternate embodiment, drug delivery device 102 may also include an optional second reservoir 124-2 and second drive mechanism 125-2 which enables the independent delivery of two different liquid drugs. As an example, reservoir 124 may be filled with insulin, while reservoir 124-2 may be filled with Pramlintide or GLP-1. In some embodiments, each of reservoirs 124, 124-2 may be configured with a separate drive mechanism 125, 125-2, respectively, which may be separately controllable by controller 121 under the direction of MDA 129. Both reservoirs 124, 124-2 may be connected to a common needle/cannula 186.

Drug delivery device 102 may be optionally configured with a user interface 127 providing a means for receiving input from the user and a means for outputting information to the user. User interface 127 may include, for example, light-emitting diodes, buttons on a housing of drug delivery device 102, a sound transducer, a micro-display, a microphone, an accelerometer for detecting motions of the device or user gestures (e.g., tapping on a housing of the device) or any other type of interface device that is configured to allow a user to enter information and/or allow drug delivery device 102 to output information for presentation to the user (e.g., alarm signals or the like).

Drug delivery device 102 includes a patient interface 186 for interfacing with the user to deliver the liquid drug. Patient interface may be, for example, a needle or cannula for delivering the drug into the body of the user (which may be done subcutaneously, intraperitoneally, or intravenously). Drug delivery device 102 further includes a mechanism for inserting the needle/cannula 186 into the body of the user, which may be integral with or attachable to drug delivery device 102. The insertion mechanism may comprise, in one embodiment, an actuator that inserts the needle/cannula 186 under the skin of the user and thereafter retracts the needle, leaving the cannula in place.

In one embodiment, drug delivery device 102 includes a communication interface 126, which may be a transceiver that operates according to one or more radio-frequency protocols, such as Bluetooth®, Wi-Fi, near-field communication, cellular, or the like. The controller 121 may, for example, communicate with user device 105 and an analyte sensor 108 via the communication interface 126.

In some embodiments, drug delivery device 102 may be provided with one or more sensors 184. The sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between the patient interface 186 and reservoir 124. The pressure sensor may be coupled to or integral with the actuator for inserting the patient interface 186 into the user. In an example, the controller 121 may be operable to determine a rate of drug infusion based on the indication of the fluid pressure. The rate of drug infusion may be compared to an infusion rate threshold, and the comparison result may be usable in determining an amount of insulin onboard (IOB) or a total daily insulin (TDI) amount. In one embodiment, analyte sensor 108 may be integral with drug delivery device 102.

Drug delivery device 102 further includes a power source 128, such as a battery, a piezoelectric device, an energy harvesting device, or the like, for supplying electrical power to controller 121, memory 123, drive mechanisms 125 and/or other components of drug delivery device 102.

Drug delivery device 102 may be configured to perform and execute processes required to deliver doses of the medication to the user without input from the user device 105 or the optional accessory device 106. As explained in more detail, MDA 129 may be operable, for example, to determine an amount of insulin to be delivered, IOB, insulin remaining, and the like and to cause controller 121 to activate drive mechanism 125 to deliver the medication from reservoir 124. MDA 129 may take as input data received from the analyte sensor 108 or from user app 160.

The reservoirs 124, 124-2 may be configured to store drugs, medications or therapeutic agents suitable for automated delivery, such as insulin, Pramlintide, GLP-1, co-formulations of insulin and GLP-1, morphine, blood pressure medicines, chemotherapy drugs, fertility drugs or the like.

Drug delivery device 102 may be a wearable device and may be attached to the body of a user, such as a patient or diabetic, at an attachment location and may deliver any therapeutic agent, including any drug or medicine, such as insulin or the like, to a user at or around the attachment location. A surface of drug delivery device 102 may include an adhesive to facilitate attachment to the skin of a user.

When configured to communicate with an external device, such as the user device 105 or the analyte sensor 108, drug delivery device 102 may receive signals over the wired or wireless link 194 from the user device 105 or from the analyte sensor 108. The controller 121 of drug delivery device 102 may receive and process the signals from the respective external devices as well as implementing delivery of a drug to the user according to a diabetes treatment plan or other drug delivery regimen.

Accessory Device

Optional accessory device 107 may be, a wearable smart device, for example, a smart watch (e.g., an Apple Watch®), smart eyeglasses, smart jewelry, a global positioning system-enabled wearable, a wearable fitness device, smart clothing, or the like. Similar to user device 105, the accessory device 107 may also be configured to perform various functions including controlling drug delivery device 102. For example, the accessory device 107 may include a communication interface 174, a processor 171, a user interface 178 and a memory 173. The user interface 178 may be a graphical user interface presented on a touchscreen display of the smart accessory device 107. The memory 173 may store programming code to operate different functions of the smart accessory device 107 as well as an instance of the user app 160, or a pared-down version of user app 160 with reduced functionality. In some instances, accessory device 107 may also include sensors of various types.

Analyte Sensor

The analyte sensor 108 may include a controller 131, a memory 132, a sensing/measuring device 133, an optional user interface 137, a power source/energy harvesting circuitry 134, and a communication interface 135. The analyte sensor 108 may be communicatively coupled to the processor 151 of the management device 105 or controller 121 of drug delivery device 102. The memory 132 may be configured to store information and programming code 136.

The analyte sensor 108 may be configured to detect multiple different analytes, such as glucose, lactate, ketones, uric acid, sodium, potassium, alcohol levels or the like, and output results of the detections, such as measurement values or the like. The analyte sensor 108 may, in an exemplary embodiment, be configured to measure a blood glucose value at a predetermined time interval, such as every 5 minutes, every 1 minute, or the like. The communication interface 135 of analyte sensor 108 may have circuitry that operates as a transceiver for communicating the measured blood glucose values to the user device 105 over a wireless link 195 or with drug delivery device 102 over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof.

Similar to the controller 121 of drug delivery device 102, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1A as separate from drug delivery device 102, in various embodiments, the analyte sensor 108 and drug delivery device 102 may be incorporated into the same unit. That is, in various examples, the analyte sensor 108 may be a part of and integral with drug delivery device 102 and contained within the same housing as drug delivery device 102 or an attachable housing thereto. In such an example configuration, the controller 121 may be able to implement the functions required for the proper delivery of the medication alone without any external inputs from user device 105, the cloud-based services 111, another sensor (not shown), the optional accessory device 106, or the like.

Cloud-Based Services

Drug delivery system 100 may communicate with or receive services from cloud-based services 111. Services provided by cloud-based services 111 may include data storage that stores personal or anonymized data, such as blood glucose measurement values, historical IOB or TDI, prior carbohydrate-compensation dosage, and other forms of data. In addition, the cloud-based services 111 may process anonymized data from multiple users to provide generalized information related to TDI, insulin sensitivity, IOB and the like. The communication link 115 that couples the cloud-based services 111 to the respective devices 102, 105, 106, 108 of system 100 may be a cellular link, a Wi-Fi link, a Bluetooth® link, or a combination thereof.

Communication Links

The wireless communication links 115 and 191-196 may be any type of wireless link operating using known wireless communication standards or proprietary standards. As an example, the wireless communication links 191-196 may provide communication links based on Bluetooth®, Zigbee®, Wi-Fi, a near-field communication standard, a cellular standard, or any other wireless protocol via the respective communication interfaces 126, 135, 154 and 174.

Operational Example

In an operational example, user application 160 implements a graphical user interface that is the primary interface with the user and is used to start and stop drug delivery device 102, program basal and bolus calculator settings for manual mode as well as program settings specific for automated mode (hybrid closed-loop or closed-loop).

User app 160, provides a graphical user interface 158 that allows for the use of large text, graphics, and on-screen instructions to prompt the user through the set-up processes and the use of system 100. It will also be used to program the user's custom basal insulin delivery profile, check the status, of drug delivery device 102, initiate bolus doses of insulin, make changes to a patient's insulin delivery profile, handle system alerts and alarms, and allow the user to switch between automated mode and manual mode.

User app 160 may configured to operate in a manual mode in which user app 160 will deliver insulin at programmed basal rates and bolus amounts with the option to set temporary basal profiles. The controller 121 will also have the ability to function as a sensor-augmented pump in manual mode, using sensor glucose data provided by the analyte sensor 108 to populate the bolus calculator.

User app 160 may configured to operate in an automated mode in which user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 for insulin dosing parameters. The insulin dosing parameters will be adapted over time based on the total daily insulin (TDI) delivered during each use of drug delivery device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

The user app 160 (or MDA 129) may provide periodic insulin micro-boluses based upon past glucose measurements and/or a predicted glucose over a prediction horizon (e.g., 60 minutes). Optimal post-prandial control may require the user to give meal boluses in the same manner as current pump therapy, but normal operation of the user app 160 will compensate for missed meal boluses and mitigate prolonged hyperglycemia. The user app 160 uses a control-to-target strategy that attempts to achieve and maintain a set target glucose value, thereby reducing the duration of prolonged hyperglycemia and hypoglycemia.

In some embodiments, user device 105 and the analyte sensor 108 may not communicate directly with one another. Instead, data (e.g., blood glucose readings) from analyte sensor may be communicated to drug delivery device 102 via link 196 and then relayed to user device 105 via link 194. In some embodiments, to enable communication between analyte sensor 108 and user device 105, the serial number of the analyte sensor must be entered into user app 160.

User app 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (JOB). IOB is estimated by user app 160 taking into account any manual bolus and insulin delivered by the algorithm.

Description of Embodiments

Figure 2A:
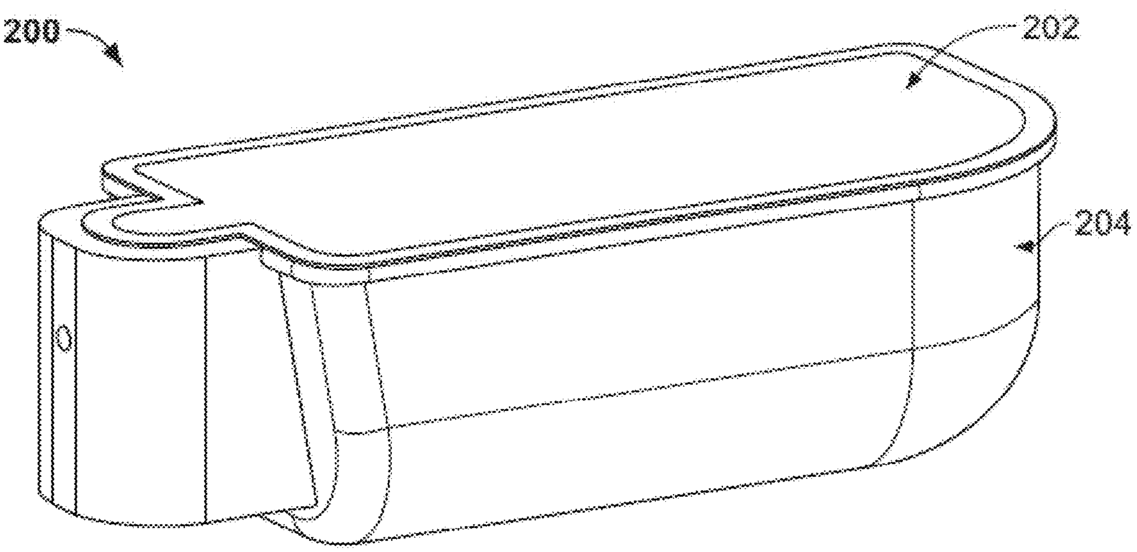
FIGS. 2A-B are a perspective view and a cross-sectional view respectively of a first embodiment of the invention showing a rigid-body reservoir having a vacuum seal.
Figure 2B:
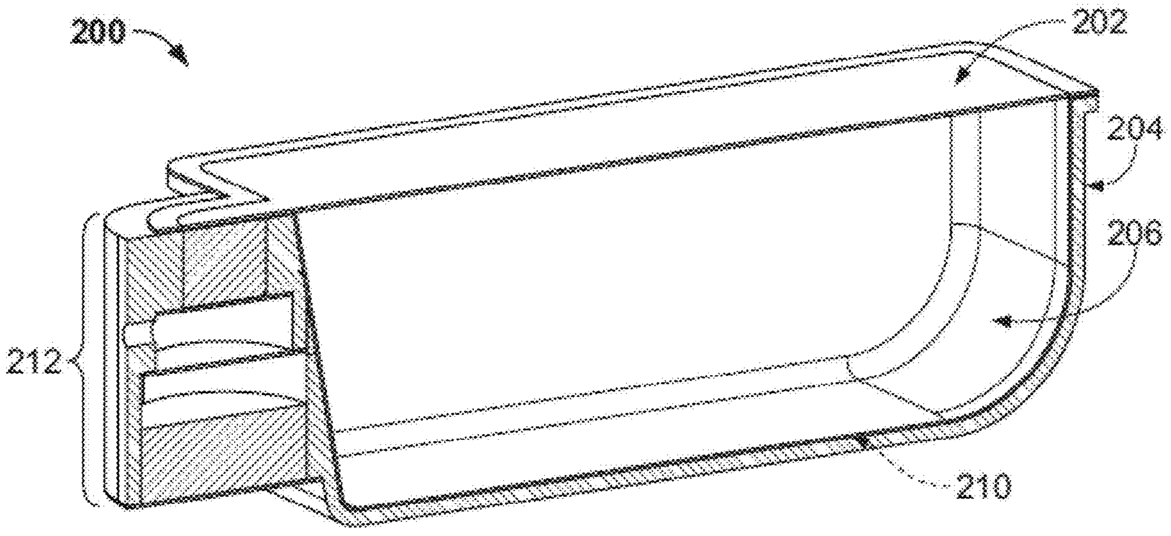

FIGS. 2A-B show a first embodiment and in the invention. The objective of this embodiment is to maintain a vacuum in the reservoir of the drug delivery device 100 during the pendency of the shelf life of the device. FIG. 2A is a perspective view of the exterior of the device, while FIG. 2B is a cross-sectional view showing the interior of the device. In this embodiment, reservoir 200 is provided with a rigid shell 204 with foil lining 206. Preferably foil lining 206 is of a material that is highly resistant to air permeating the foil. In this embodiment, a vacuum 210 is formed between rigid shell 204 and foil lining 206 and will become the area which holds the liquid drug after the reservoir 200 is filled by the user. As the reservoir is filled, the liquid drug enters the vacuum area 210 between foil lining 206 and rigid shell 204, thereby compressing the foil lining 206 and displacing it away from rigid shell 204. The liquid drug then occupies the area formed by the displaced foil lining 206.

In certain embodiments, reservoir 200 may be provided with a barrier film 202 covering the open face of the reservoir 200. In this embodiment, barrier film 202 is included as an extra precaution in the event that the oxygen permeability of foil lining 206 is too high to hold a vacuum between lining 206 and rigid shell 204 for the duration of the pendency of the shelf life of device 100.

Figure 2C:
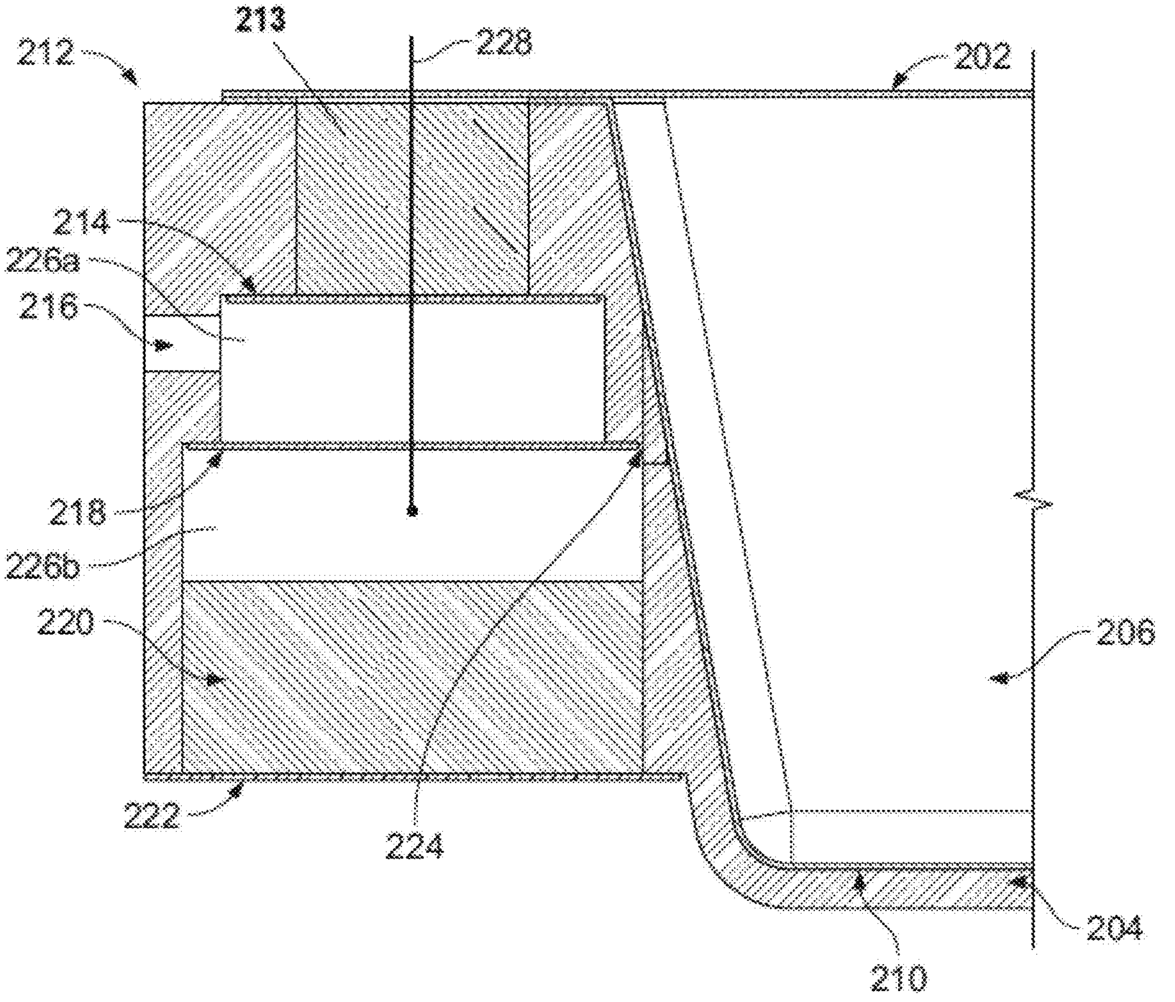
FIG. 2C is a close-up, cross-sectional view of the fill port of the embodiment of FIGS. 2A-B, showing placement of the barrier films and septa that maintain the vacuum in the reservoir prior to the filling of the device with the liquid drug.

In this embodiment, reservoir 200 may be provided with fill mechanism 212, shown in detail in FIG. 2C. Fill mechanism 212 is provided with an inlet 224 to the reservoir 200 which is open on one end to space 210 between foil lining 206 and rigid shell 204. On the other end, inlet 224 is in fluid communication with area 226 *b*. Area 226 *b* is sealed from outside air pressure by barrier film 218 and septum 220. An additional barrier film 222 may be provided on the other side of septum 220 to provide for the protection for vacuum area 210 from outside air pressure. Area 226 *b* is separated from area 226 *a* by barrier film 218. Area 226 *a* is in fluid communication with outlet port 216.

In operation, when the user wishes to fill reservoir 200 with a liquid drug, a fill needle is inserted to the position shown with reference number 228 in FIG. 2C. The insertion of the needle pierces barrier 202, and the needle passes through septum 213, punctures barrier film 214, passes through area 226*a*, punctures barrier film 218 and is positioned in area 226*b*. As the liquid drug flows through the fill needle into area 226*b*, it enters inlet 224 and begins to fill the vacuum 210 between displaced areas of foil lining 206 and rigid shell 204. In the process, lining 206 is displaced from rigid shell 204 only enough to accommodate the liquid drug, thereby maintaining vacuum 210.

Once the reservoir is full, the needle is withdrawn and barrier film 218 remains punctured such as to provide fluid communication between area 226*b* and area 226*a* through the puncture in barrier film 218. Thus, a liquid drug is able to flow from the vacuum 210, through areas 226*b* and 226*a* and ultimately to outlet 216 to a pump mechanism of the device 100. Septum 213, self-seals when the fill needle is extracted and creates a seal for area 226*a*, thereby preventing the liquid drug from escaping area 226*a* during operation of the device 100. Preferably, the pump mechanism provides a suction which will draw the liquid drug from vacuum area 210 to outlet 216.

Figure 3A:
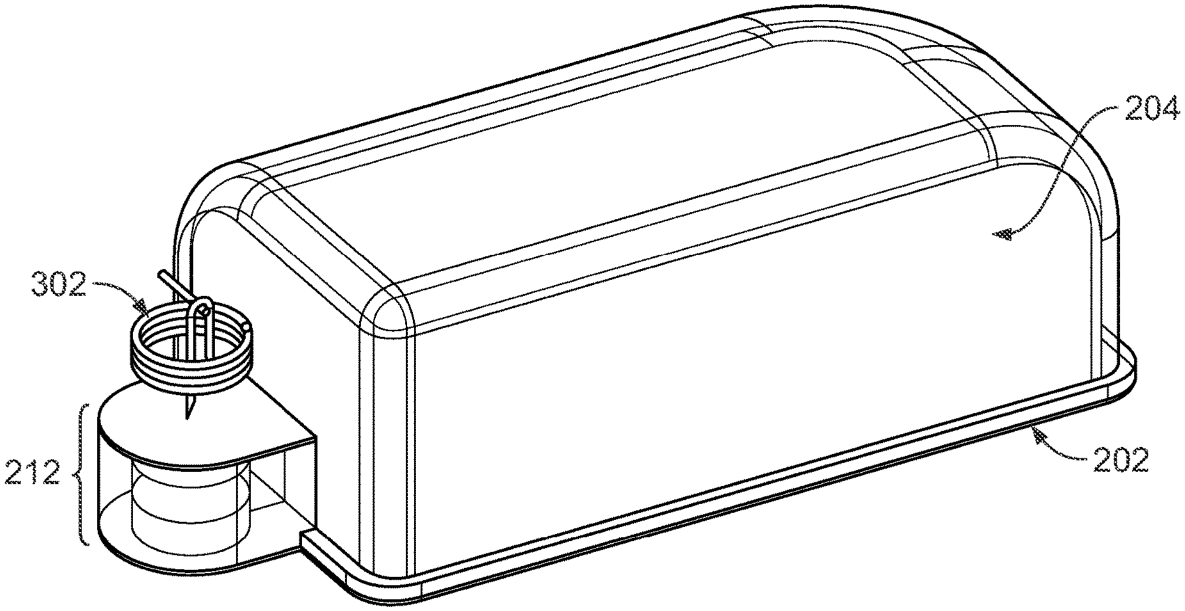
FIGS. 3A-B are a perspective view and a cross-sectional view, respectively, of a variation of the embodiment of FIGS. 2A-B in which a spring-loaded fill needle is used to puncture the seals when filling the reservoir with the liquid drug.
Figure 3B:
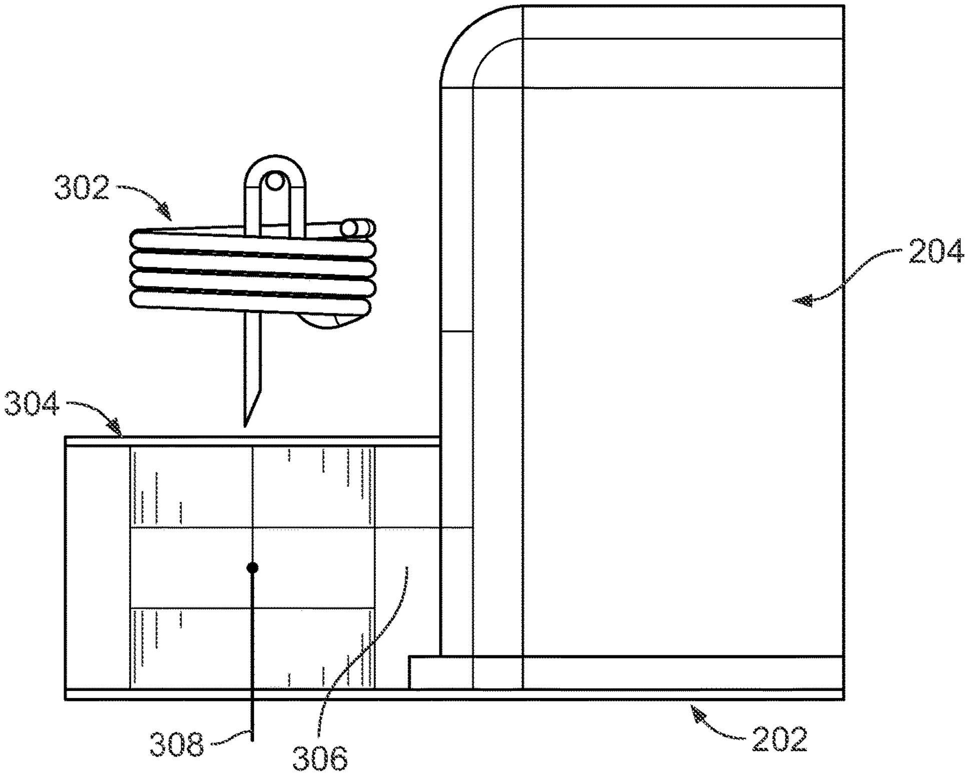

FIGS. 3A-B show a variation of the embodiment of FIGS. 2A-C in which the fill needle is provided as a spring mechanism which, when released, automatically positions fill needle to position 228 as shown in FIG. 2C. One advantage of this embodiment is a decrease in the risk of user error because the reservoir outlet is open by a mechanism rather by than by an action of the user. In this embodiment, the needle, when released, is inserted to position 308 via the spring mechanism 302. The liquid drug can then enter reservoir 204 via inlet 406. In some embodiments, fill structure 212 may be the same fill structure as shown in the embodiment of FIGS. 2A-C.

Figure 4:
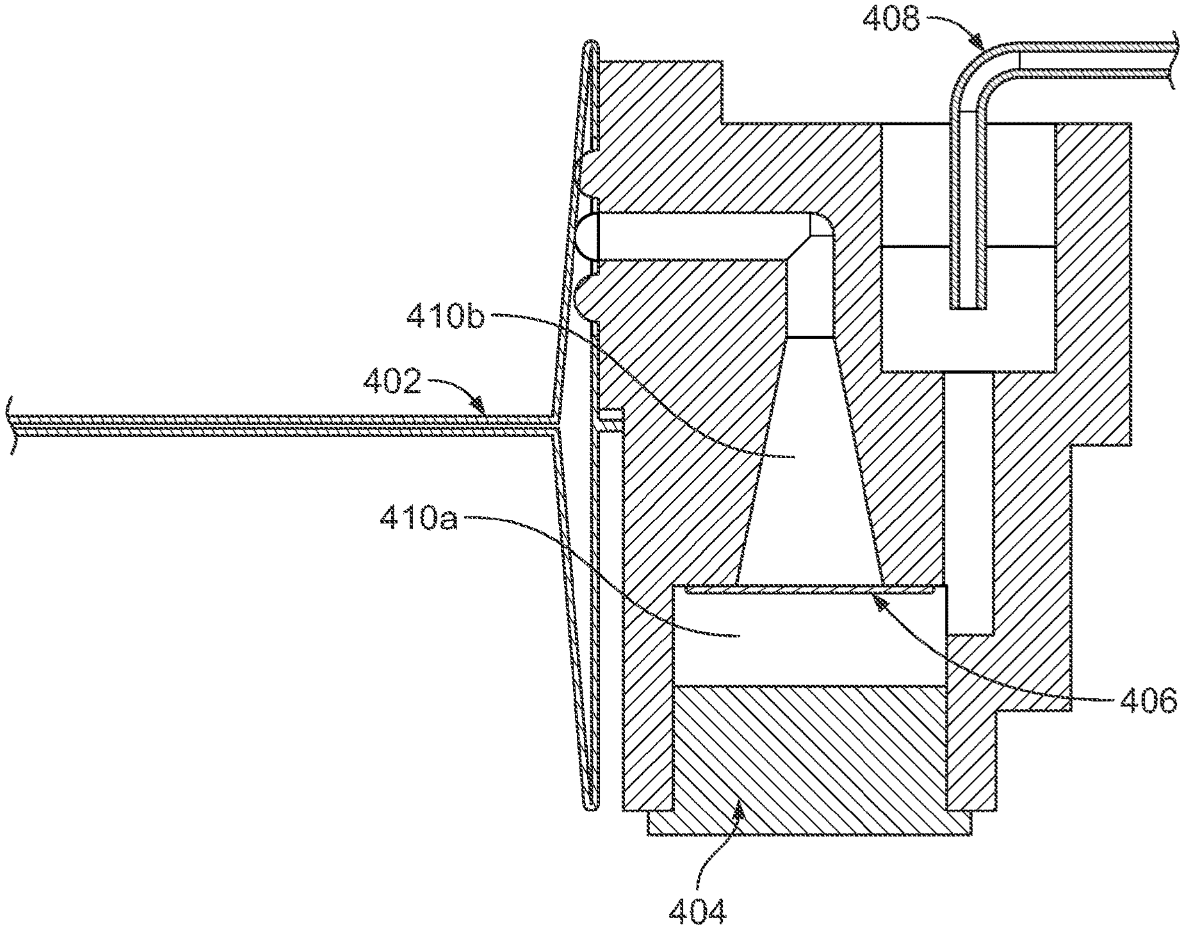
FIG. 4 is a cross-sectional view of an alternative embodiment having a collapsible reservoir.

FIG. 4 shows a variation of the embodiment of FIGS. 2A-C. In the embodiment of FIG. 4, reservoir 402 is provided as a collapsible structure or liner, preferably composed of foil or another material which is impermeable to air. During the manufacturing process of the device, reservoir 402 is compressed such as to void all air from within the reservoir. Additionally, during the manufacturing process, reservoir 402 may be exposed to a vacuum to completely evacuate all air from within reservoir 402. Additionally, the liner or material of reservoir 402 may be subjected to electrostatic forces to cause the material of reservoir 402 to be attracted to itself, thereby ensuring that no air is within reservoir 402. These electrostatic forces may be created during the manufacturing process, such as by having the material of reservoir 402 travel over one or more metal rollers. As more metal rollers are used, additional static electricity may be imparted to reservoir 402. FIG. 4 shows a small air gap on the right-hand side of reservoir 402 to better show the different surfaces of reservoir 402, but this air gap may be non-existent in practice, such that all interior surfaces of reservoir 402 are touching another interior surface of reservoir 402, through electrostatic forces, a vacuum, a partial (temporary/breakable) welding of two cross-surfaces together, or otherwise, and no air is present within reservoir 402.

The fill mechanism for the embodiment of FIG. 4 comprises a structure having an open area 410*a* isolated from the outside by septum 404. Open area 410*a* is in fluid communication with the outlet 408, which may be connected to a pump mechanism for drawing the liquid drug from the reservoir. Area 410*a* is isolated from area 410*b* by barrier film 406. During the filling process, the fill needle is inserted through septum 404, through area 410*a* and into area 410*b*, thereby puncturing barrier film 406. Area 410*b* may be conical in shape to guide the fill needle into the proper position and may be configured with a right-angle fluid path to prevent the fill needle from being inserted too far and puncturing reservoir 402. As a liquid drug is forced from the fill needle into reservoir 402, reservoir 402 expands to accommodate the liquid drug, thereby maintaining the vacuum within reservoir 402. Once the fill needle has been removed, the puncture in barrier film 406 allows fluid communication between the reservoir, area 410*b*, area 410*a* and outlet 408 to the pump mechanism. Area 410*a* remains otherwise sealed from the outside by septum 404.

Figure 5A:
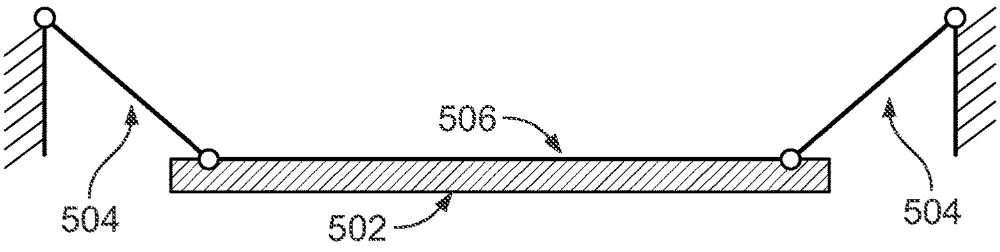
FIG. 5A-C show an embodiment of the invention using a bi-stable hinge mechanism which moves a rigid plate between first and second stable positions during filling of the reservoir.
Figure 5B:
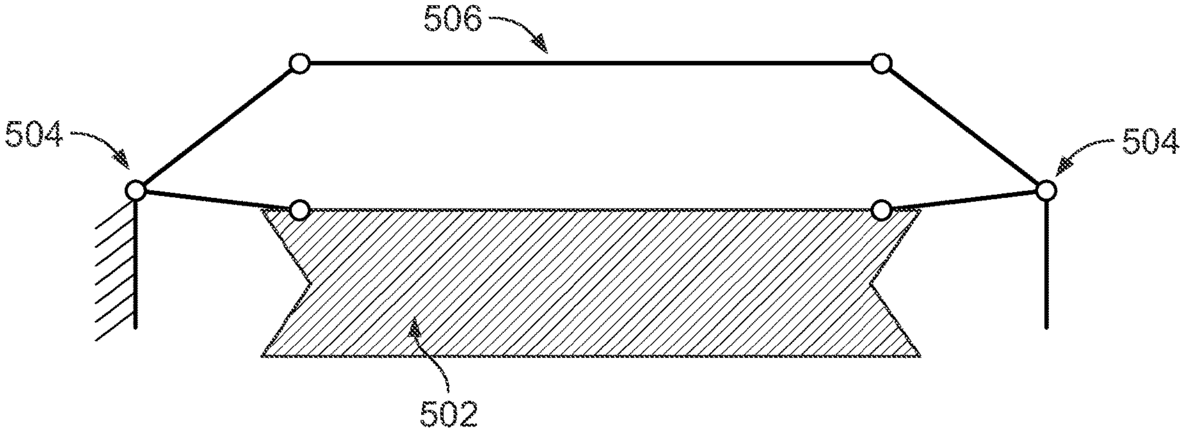
Figure 5C:
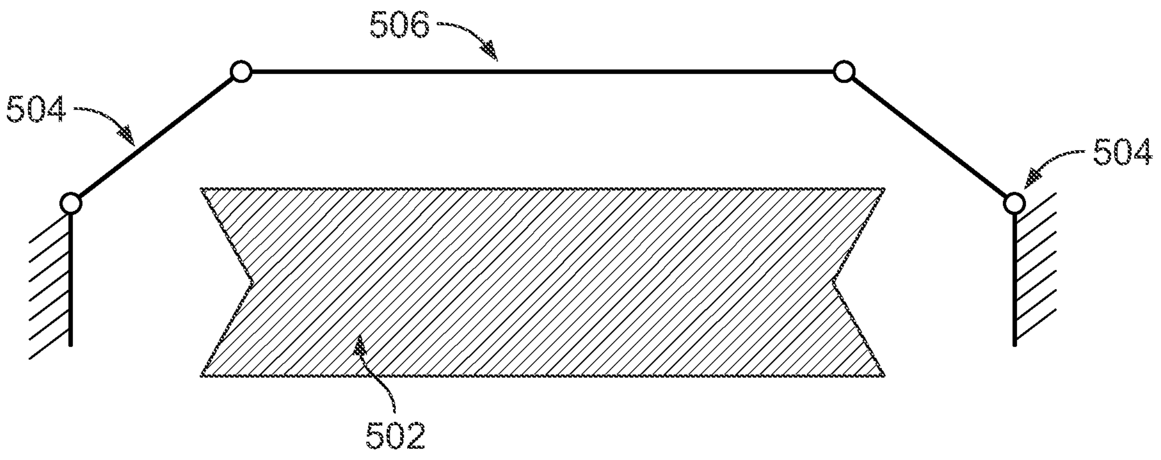
Figure 6A:
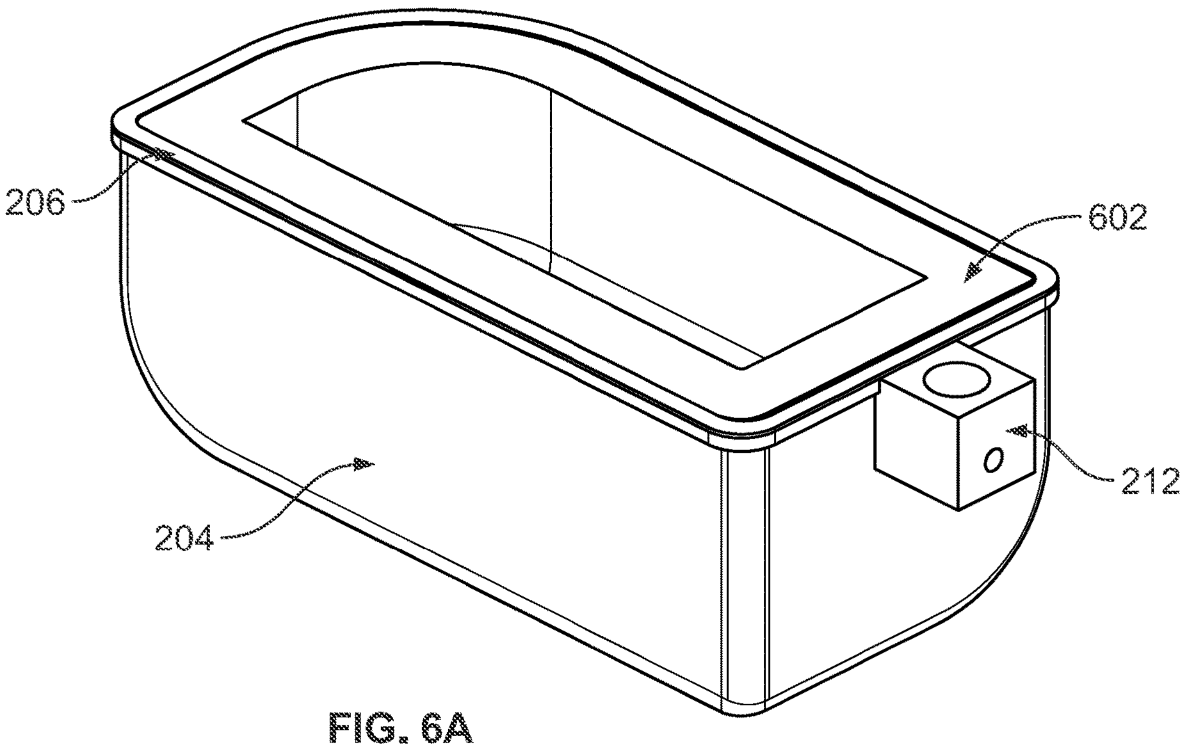
FIG. 6A-B are a perspective view and a cross-sectional perspective view, respectively, of yet another embodiment of the invention wherein a crushable or displaceable material provides support for maintaining contact between the walls of a rigid reservoir and a foil lining of the reservoir.
Figure 6B:
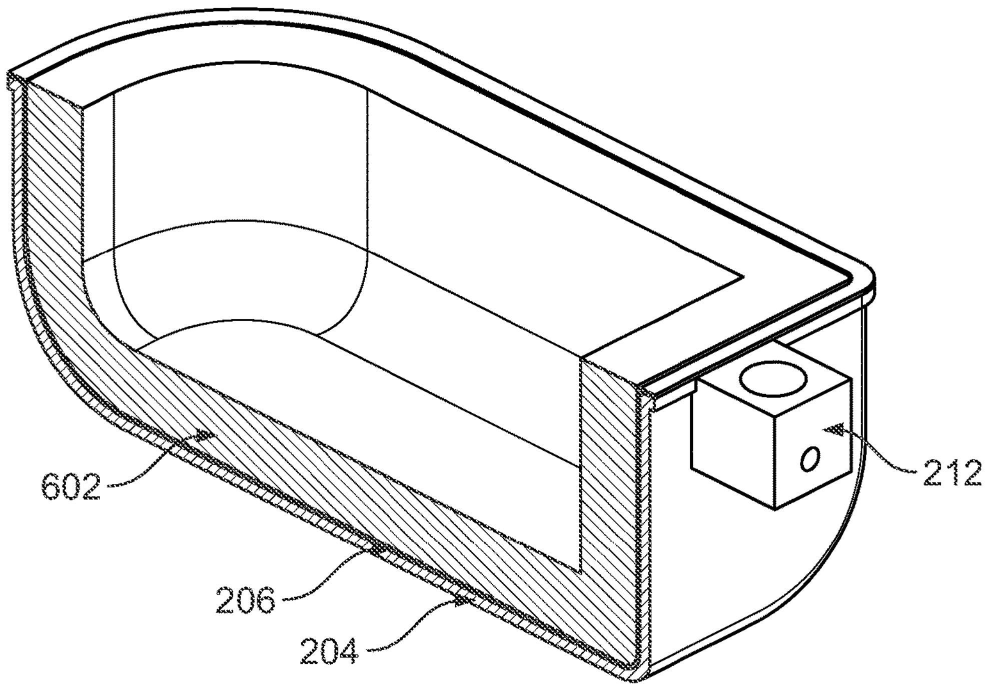

FIGS. 5A-C show another embodiment of the invention in which a collapsible reservoir 502 is utilized. As shown in FIG. 5A, during the shelf life of the device 100 reservoir 502 is held in a fully collapsed state by a rigid plate 506 controlled by two bi-stable hinge 504 which, in a first stable position shown in FIG. 5A, provides a compressive force to reservoir 502 by forcing rigid plate 506 onto reservoir 502, thereby preventing air from entering reservoir 502 during the shelf life of device 100. FIG. 5B shows reservoir 502 in a partially filled state. As reservoir 502 becomes filled with a liquid drug, it expands, thereby forcing rigid plate 506 upward from the first stable position toward a second stable position of bi-stable hinge 504. When the rigid plate 506 has reached a critical position by the expansion of reservoir 502, the bi-stable hinges 504 snaps the rigid plate 506 into the second stable position of bi-stable hinges 504, shown in FIG. 5C. Rigid plate 506 thereafter remains in the second stable position of the bi-stable hinges 504 thereby allowing reservoir 502 to be filled or collapsed through normal operation of device 100. It should be noted that the embodiment shown in FIGS. 5A-C could readily be adapted for use with the embodiment of FIG. 3, which also uses a collapsible reservoir FIGS. 6A-B show yet another embodiment of the invention. In this embodiment, as with the embodiment shown in FIGS. 2A-B, the reservoir comprises a rigid shell 204 lined with a foil liner 206. Foil liner 206 is supported by a support structure/material 602, which provides support for foil liner 206 and prevents air from entering the space between rigid shell 204 and foil liner 206. This embodiment may be fitted with the same fill structure 212 shown in FIG. 2C. In this embodiment, as the user fills the reservoir, the liquid drug will push the foil liner 206 away from the rigid shell 204 and in the process will displace all or a portion of support structure 602. In preferred embodiments of the invention, support structure 602 may comprise, for example, a crushable foam or other material that is strong enough to provide rigid support for foil liner 206 when the reservoir is empty but which may be displaced by the pressure of the liquid drug entering the space between foil liner 206 and outer shell 204. In other embodiments, support structure 602 may be a material that is sprayed onto liner 206 to (temporarily) keep liner 206 directly in contact with rigid shell 204, until a force is imparted by a liquid drug inserted between liner 206 and rigid shell 204. Upon insertion of a liquid drug, the liner 206 displaces support structure 602 and may cause support structure 602 to crumble or break off. Remains of support structure 602 may remain within an interior portion of rigid shell 204, but not go between rigid shell 204 and liner 206. The support structure or material 602 shown in FIGS. 6A-6B are shown with an exaggerated thickness to better show the material and its position/orientation with respect to liner 206 and rigid shell 204 prior to being displaced upon insertion of a liquid drug into the reservoir.

Figure 7A:
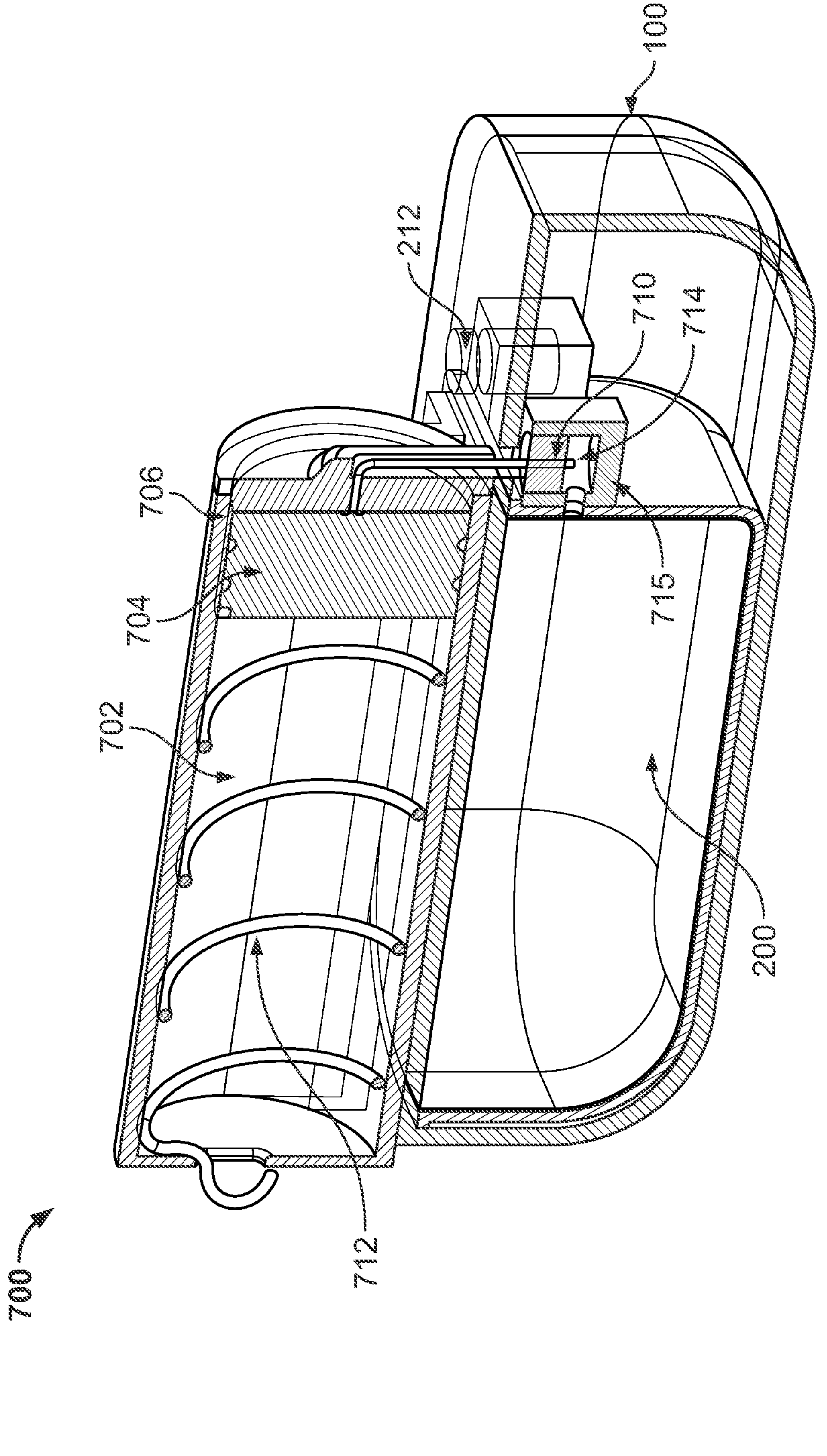
FIG. 7A-C show various views of an embodiment of the second aspect of the invention showing a mechanism for evacuating air from the reservoir prior to filling.
Figure 7B:
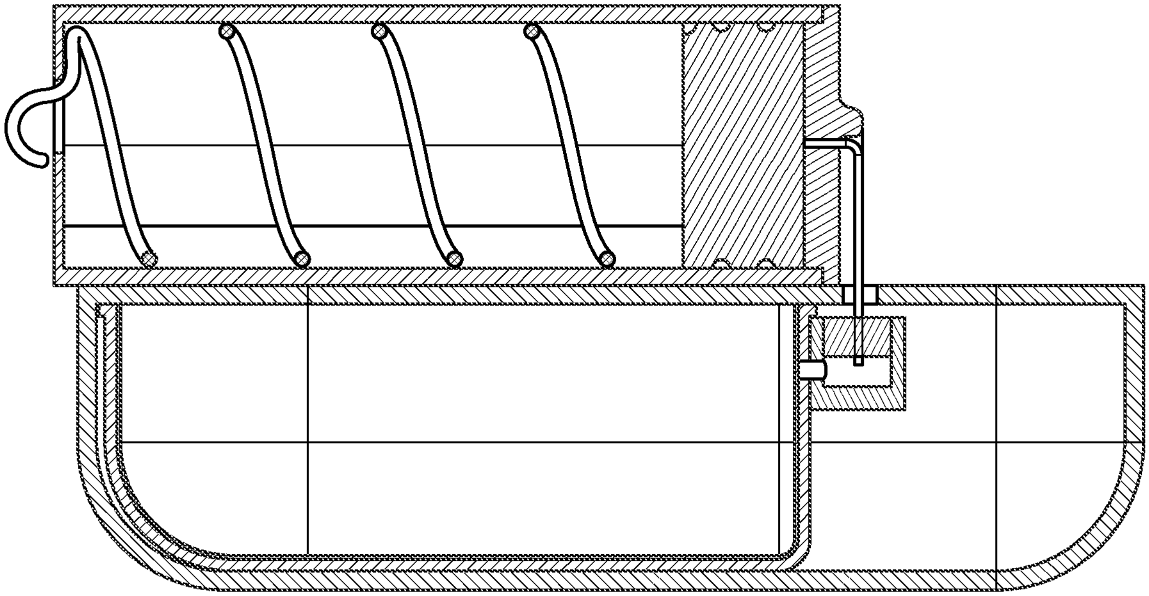
Figure 7C:
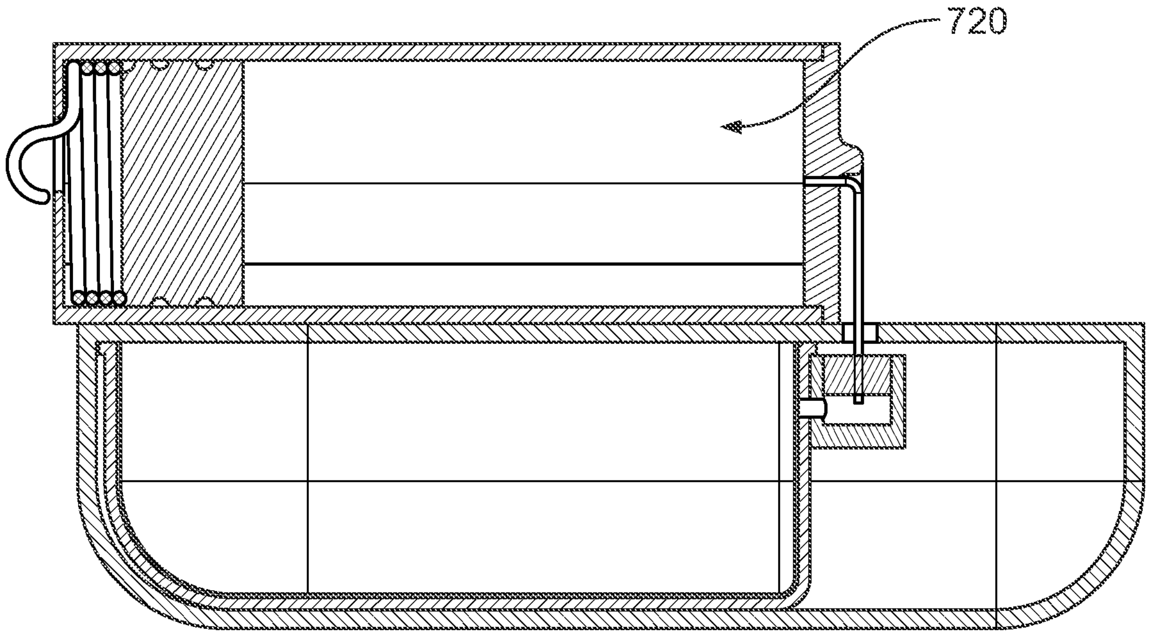

In embodiments directed to the second aspect of the invention, the drug delivery device 100 may be provided with an apparatus 700 temporarily attached to the external surface of the housing of the drug delivery device 100. A cross-sectional isometric view of apparatus 700 is shown in FIG. 7A. In this embodiment, the reservoir may be reservoir 200 shown in FIGS. 2A-B. The apparatus 700 consists of an air chamber 702 with a spring-loaded plunger 704 inside. Extension spring 712 is attached to plunger 704 and to the back of air chamber 702 and is designed to pull plunger 704 toward the rear of air chamber 702 when released. An air pathway 710 attaches the air chamber 702 to reservoir 200 inside the drug delivery device 100. In some embodiments, air pathway 710 may be, for example, a needle which pierces septum 714, thereby allowing fluid communication between air chamber 702 and reservoir 200 via needle 710. In the initial position, shown in FIG. 7B, there is little to no space between the plunger 704 and the front of the air chamber 702. When activated (for example, upon opening the packaging of drug delivery device 100) a release mechanism (not shown) will be triggered, thereby releasing plunger 704 and causing extension spring 702 to draw plunger 704 toward the rear of air chamber 702, until reaching a position shown in FIG. 7C.

This causes any residual air remaining in reservoir 200 to be drawn from reservoir 200 into the air chamber 702. The user must then remove the apparatus 700 from the housing of drug delivery device 100 prior to filling reservoir 200 with the liquid drug. Apparatus 700 may be provided with a breakaway connection that allows apparatus 700 to be removed from the housing of drug delivery device 100 with a pulling or twisting motion that will break the connection. As apparatus 700 is removed from drug delivery device 100, the needle 710 attaching the air chamber 702 to reservoir 200 will be removed with the apparatus 700, and a septum 714 on the reservoir side will self-seal. Reservoir 200 may be fitted with fill port 212 essentially identical to that shown in FIG. 2C which may be used by the user to fill the reservoir 200 with a liquid drug as described with respect to the embodiment of FIGS. 2A-C. The structure 715 used for the fluid attachment of apparatus 702 reservoir 200 may be integrated with fill structure 212 or may be provided as a separate structure on the external surface of reservoir 200.

The following examples pertain to further embodiments:

Example 1 is a reservoir comprising a rigid shell, a foil lining disposed on an interior surface of the rigid shell, an inlet port in fluid communication with a space between the foil lining and the rigid shell and a fill structure in fluid communication with the inlet port.

Example 2 is an extension of Example 1, or any other example disclosed herein, wherein the fill structure comprises a septum, a first space adjacent to the septum in fluid communication with an outlet port, a second space in fluid communication with an inlet port and a barrier film separating the first and second spaces.

Example 3 is an extension of Example 2, or any other example disclosed herein, wherein the reservoir further comprises a second barrier film separating the first space and the septum.

Example 4 is an extension of Example 3, or any other example disclosed herein, wherein the reservoir further comprises a second septum located adjacent the second space and a second barrier film adjacent to the second septum.

Example 5 in an extension of Example 1, or any other example disclosed herein, wherein the reservoir further comprises a sealing barrier film covering the rigid shell and the fill structure.

Example 6 is an extension of Example 2, or any other example disclosed herein, wherein the fill needle is a spring-loaded fill needle.

Example 7 is an extension of Example 1, or any other example disclosed herein, further comprising a collapsible support structure for holding the foil lining against the rigid shell.

Example 8 is an extension of Example 7, or any other example disclosed herein, wherein the collapsible support structure comprises a compressible foam.

Example 9 is a reservoir comprising a collapsible container and a fill structure in fluid communication with the collapsible container.

Example 10 is an extension of Example 9, or any other example disclosed herein, wherein the fill structure comprises first and second internal spaces separated by a barrier film and a septum defining one side of the first internal space.

Example 11 is an extension of Example 10, or any other example disclosed herein, wherein in a fill needle inserted through the septum into the second internal space allows movement of a liquid drug into the collapsible container.

Example 12 is an extension of Example 10, or any other example disclosed herein, wherein fluid communication is enabled between the first and second internal spaces via the punctured barrier film when the fill needle has been removed.

Example 13 is an extension of Example 12, or any other example disclosed herein, wherein the liquid drug expands the collapsible container as the liquid drug is introduced into the collapsible container through the fill needle.

Example 14 is a reservoir comprising a collapsible container and a bi-stable hinge which moves a rigid plate between a first stable position and a second stable position.

Example 15 is an extension of Example 14, or any other example disclosed herein, wherein filling the collapsible reservoir pushes the rigid plate from the first stable position toward the second stable position until rigid plate reaches a position wherein the bi-stable hinge snaps rigid plate into the second stable position.

Example 16 is a mechanism for removing air from a reservoir comprising an air chamber, a spring-loaded plunger disposed within the air chamber, an air pathway allowing fluid communication between the air chamber and the reservoir of a drug delivery device and a release mechanism for releasing the spring-loaded plunger.

Example 17 is an extension of Example 16, or any other example disclosed herein, wherein the plunger, when released, moves away from the air pathway and toward the distal end of the air chamber thereby drawing air from the reservoir into the air chamber.

Example 18 is an extension of Example 17, or any other example disclosed herein, where the mechanism is detachable from the reservoir and further comprises a septum for sealing the reservoir when the air pathway is removed as a mechanism is detached from the reservoir.

Example 19 is an extension of Example 16, or any other example disclosed herein, wherein the air pathway comprises a needle.

Example 20 is an extension of Example 16, or any other example disclosed herein, wherein the reservoir is disposed within a housing of drug delivery device and the mechanism is disposed external to the housing of the drug delivery device and wherein the air pathway extends through the housing of the drug delivery device.

Example 21 is an extension of Example 20, or any other example disclosed herein, wherein the mechanism is attached to the drug delivery device via a breakaway connection which when broken allows removal of the mechanism from the housing of the drug delivery device.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Certain embodiments of the present invention were described above. It is, however, expressly noted that the present invention is not limited to those embodiments, but rather it is intended that additions and modifications to the expressly described embodiments herein are also to be included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. As such, the invention is not to be defined only by the preceding illustrative description. Future filed applications claiming priority to this application may claim the disclosed subject matter in a different manner and may generally include any set of one or more limitations as variously disclosed or otherwise demonstrated herein.

The invention claimed is:

1. A reservoir comprising:
a rigid shell;
a lining disposed on an interior surface of the rigid shell;
an inlet port in fluid communication with a space between the lining and the rigid shell;
a fill structure in fluid communication with the inlet port;
a septum;
a first space adjacent to septum, the first space in fluid communication with an outlet port;
a second space in fluid communication with the inlet port; and
a barrier film separating the first and second spaces.

2. The reservoir of claim 1 further comprising:
a second barrier film separating the first space and the septum;
wherein the second barrier film is pierced when a fill needle is introduced into the second space.

3. The reservoir of claim 2 further comprising:
a second septum located adjacent the second space opposite the barrier film,
wherein the second barrier film is adjacent to the second septum opposite the second space.

4. The reservoir of claim 1 wherein:
the fill needle comprises a spring-loaded fill needle external to the reservoir; and
releasing the spring-loaded fill needle causes fill needle to extend into the second space.

5. The reservoir of claim 2 further comprising:
a sealing barrier film covering the rigid shell and the fill structure.

6. The reservoir of claim 1 further comprising:
a collapsible support structure for holding the lining against the rigid shell;
wherein filling the space between the lining and the rigid shell with a liquid drug causes the foil lining to expand against the collapsible support structure and wherein the support structure becomes partially or fully displaced when the space between the lining and the rigid shell is filled with the liquid drug.

7. The reservoir of claim 6 were in the collapsible support structure comprises a compressible foam.

8. The reservoir of claim 1, wherein a fill needle inserted through the septum into the second space punctures the barrier film separating the first and second spaces.

9. The reservoir of claim 8, wherein a liquid drug introduced through the fill needle migrates from the second space to the space between the rigid shell and the foil lining via the inlet port.

10. The reservoir of claim 8, wherein removal of the fill needle allows fluid communication between the second space and the first space.

* * * * *